United States Patent [19]

Connery et al.

[11] 4,189,367
[45] Feb. 19, 1980

[54] METHOD FOR TESTING ION SELECTIVE ELECTRODES IN CONTINUOUS MEASURING SYSTEMS

[75] Inventors: James G. Connery, Ambler; Robert D. Jurenko; Earl W. Shaffer, Jr., both of Lansdale, all of Pa.

[73] Assignee: Leeds & Northrup Company, North Wales, Pa.

[21] Appl. No.: 952,758

[22] Filed: Oct. 19, 1978

[51] Int. Cl.² ............................................. G01N 27/46
[52] U.S. Cl. ............................... 204/195 G; 204/1 T; 204/195 M; 324/51
[58] Field of Search ............... 204/1 T, 195 R, 195 G, 204/195 M; 324/51

[56] References Cited

U.S. PATENT DOCUMENTS

| | | | |
|---|---|---|---|
| 2,117,596 | 5/1938 | Bender et al. | 204/195 G |
| 2,563,062 | 8/1951 | Perley | 204/195 G |
| 2,578,044 | 12/1951 | Coleman | 204/195 G |
| 3,661,748 | 5/1972 | Blackmer | 204/195 P |
| 3,718,568 | 2/1973 | Neuwelt | 204/195 P |

*Primary Examiner*—T. Tung
*Attorney, Agent, or Firm*—William G. Miller, Jr.; Raymond F. MacKay

[57] ABSTRACT

The membrane of an ion selective electrode is tested for damage while it is being used for continuous measurement by sending a test current through the electrode system and measuring the voltage change produced. If the voltage change does not reach the value expected with an intact high resistance electrode, a defective electrode is indicated. A reverse current of the same magnitude and duration is then sent through the electrode system.

7 Claims, 2 Drawing Figures

METHOD FOR TESTING ION SELECTIVE ELECTRODES IN CONTINUOUS MEASURING SYSTEMS

BACKGROUND OF THE INVENTION

This invention relates to a method and means for testing high impedance, ion selective electrodes while they are being used for measurement so as to determine whether or not the ion selective membrane of the electrode is damaged. It is useful to make this determination while the electrodes are being used to determine the ion activity or some property of activity such as pH, concentration, etc. of the solution being measured. In the past, it has been necessary for those who desire to make measurements of pH or sodium ion concentration, for example, to occasionally examine the electrodes when those electrodes include a high resistance membrane such as a glass membrane so as to determine whether or not the membrane was damaged as by being cracked or broken. This has been necessary since a cracked glass electrode, for example, usually provides a steady potential and thus a steady reading which gives no indication to the operator that the measurement being made is incorrect and that the electrode is defective.

It is, of course, desirable that electrode systems should not require frequent attention or examination, and that the user should be able to depend on the measurements made with them, particularly in industrial applications where they are frequently applied to the continuous measurement of process fluids. It is therefore an object of this invention to provide a method for testing of the electrodes to determine if the membrane is damaged so as to make unnecessary a visual examination of the electrode. Since the membrane of ion selective electrode systems typically have an impedance which is greater by a factor of ten than the combined impedance of the associated reference electrode and the solution being measured, it is advantageous to detect a damaged membrane by measuring the impedance of the electrode system and identifying a drop in resistance below the expected value as an indication of damage. It has been established in the prior art that the bulk resistance of a membrane such as a glass membrane can be measured by passing a unidirectional test current through the glass for a short period and measuring the voltage drop resulting from that current to thereby determine if the resistance of the glass is as high as it should be. Such measurements, however, have been only used when the ion selective electrode was not being used for continuous measurement. Such a method would not be satisfactory for electrodes applied to continuous measurements for the unidirectional current would cause polarization of the electrode, thus producing erroneous measurements. The present invention overcomes that problem.

SUMMARY OF THE INVENTION

In carrying out the present invention there is provided a method for measuring the resistance of an ion selective electrode system during its use for measurement to detect damage to the ion selective membrane. That method utilizes as a first step the passing of a first current through the electrode system. That step is followed by the passing of a second current opposite the first current through the electrode system to condition the system for further ion concentration measurements. There is also a measurement of the total change in voltage across the electrode system which results from the flow of current so that a damaged membrane will be indicated when the voltage change is less than a minimum expected for the current used.

DESCRIPTION OF THE PREFERRED EMBODIMENT

Figures 1, 2:
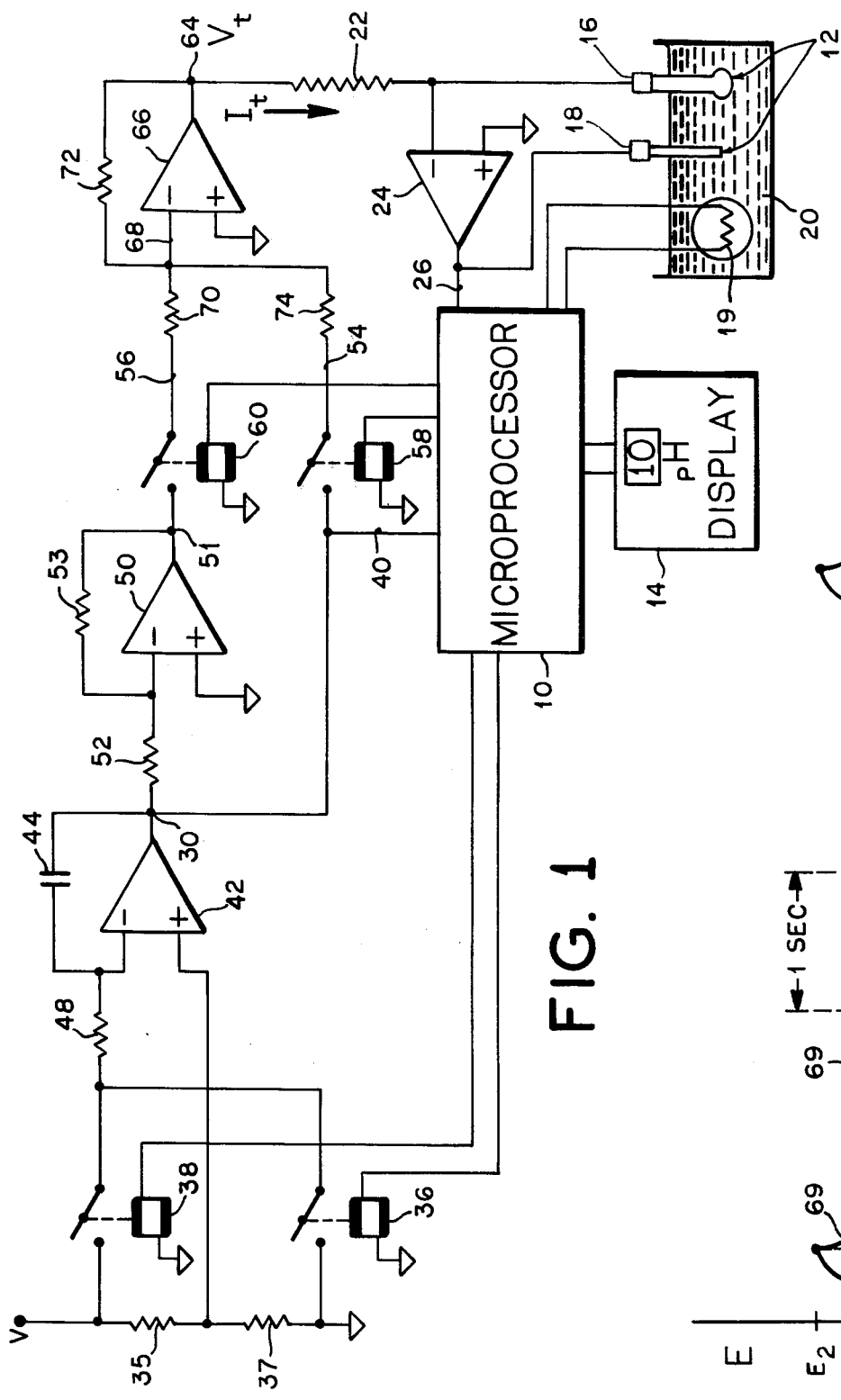
FIG. 1 is a circuit diagram of the analog circuit for carrying out the method of this invention in response to signals from a microprocessor.
FIG. 2 is a timing diagram showing the variation in the voltage output of the electrodes which occurs upon application of the test current.

In FIG. 1 there is shown a microprocessor 10 which is operable to actuate the relays in the analog circuit shown for the application of a test current to an electrode system such as the pH electrode system 12. The microprocessor 10 also provides for the measurement of the output of the electrode system 12 to produce on the digital display 14 a digital indication of the pH being measured by the electrode system 12.

As shown, the electrode system 12 includes a glass pH electrode 16, a reference electrode 18, and a thermistor temperature sensing element 19, all of which are immersed in a fluid 20 whose pH is to be measured.

If we assume that there is no test current being applied to the electrode system through resistor 22, it will be evident that the differential amplifier 24 will be effective to produce on its output line 26 a voltage corresponding to the voltage produced between the electrodes 16 and 18 so that the voltage on line 26 is indicative of the pH being measured by the electrodes 16 and 18. That voltage is then supplied to the display unit 14 which provides an indication of the magnitude of the pH being measured.

When it is desired to test the glass electrode 16 to determine if the glass membrane of the electrode is cracked or broken, then a test voltage $V_t$ is applied through resistor 22, producing a test current $I_t$. The current through resistor 22 will be nulled by a feedback current through the electrode pair 16, 18 resulting from the output voltage produced on line 26 by amplifier 24. The magnitude of the test current will preferably be determined as being that magnitude required to cause a change in voltage on line 26 which will be of at least a predetermined amount, predetermined as the criteria to indicate that an undamaged glass electrode is present.

As stated on page 56 in "Glass Electrodes for Hydrogen and Other Cations", published by Marcel Dekker, Inc., N.Y. in 1976 and edited by George Eisenman, the resistivity of the glass electrode varies with temperature in accordance with the following equation:

$$\text{resistivity} = \rho_0 \exp(\phi/kT)$$

where:
 $\phi$ is the energy barrier
 k is Boltzman's constant
 T is the absolute temperature, and
 $\rho_0$ is a pre-exponential factor.

Typically the glass membrane has a characteristic resistance in the megohm to gigohm range.

Therefore, it is important for the microprocessor to measure the temperature of the glass membrane with thermistor 19 which measures the temperature of the solution in which the glass membrane is immersed; and to then calculate the voltage desired at junction 30 of FIG. 1 to provide through resistor 22 a test current which will cause a change in emf across the electrode system of at least the predetermined magnitude when the glass electrode is intact. The microprocessor utilizes the calculated value for the voltage at junction 30 as the reference to which the potential obtained from voltage source V and resistors 35 and 37 is adjusted by selectively energizing relays 36 and 38, depending upon whether the voltage 30 needs to be increased or decreased to equal the calculated value. Thus, the microprocessor operates to compare the voltage from junction 30 as it appears on line 40 with the value calculated by the microprocessor and if, for example, the voltage at junction 30 is too low, the relay 38 is actuated for that amount of time which has been calculated as being necessary to increase the voltage 30 to its proper value by means of the integrating circuit which includes the differential amplifier 42 and capacitor 44 in conjunction with resistor 48. Similarly, if the voltage at junction 30 is too high, relay 36 will be energized to close its associated contacts and cause the integrator to decrease the voltage at junction 30. This adjustment may be carried out frequently to compensate for drift and other problems associated with voltage sources, or for changes in the temperature of the solution being measured.

The differential amplifier 50, in combination with resistors 42 and 53, is effective to invert the polarity of the potential at junction 30 so that there can be made available on the two lines 54 and 56 potentials of equal magnitude but of opposite polarity depending upon which of the relays 58 or 60 is energized by the microprocessor. Thus, with the arrangement shown, a negative test voltage can be developed at junction 30 while a positive test voltage of the same magnitude is available at the output of amplifier 50.

The microprocessor 10 is programmed to close the contacts connection junction 51 at the output of amplifier 50 with line 56 by energizing the relay coil 60 to provide a negative test current through resistor 22 by virtue of the resulting potential at junction 64 which is of equal magnitude and opposite sense to that supplied at the inverting input of amplifier 66 from line 68 as a result of the current flow from line 56 through resistor 70. The amplifier 66 is shown as having a feedback resistor 72 and another input resistor 74 which connects line 54 with line 68. With resistors 70, 72, and 74 of equal magnitude the amplification of amplifier 66 is unity.

With the application of a test current through resistor 22, which is of known value, there will appear a voltage change on line 26 which will reach a predetermined value as a minimum at the time the voltage is measured if the glass membrane of the pH electrode 16 is not cracked. The change in the voltage on line 26 during this test if the pH of the solution is constant is shown graphically by line 69 in FIG. 2 where at time $T_1$ the voltage is at a value $E_1$ corresponding to the pH of the solution 20 just prior to the application of the test current $I_t$. That voltage increases exponentially as is shown in FIG. 2 as a result of the application of a negative test current until it reaches a value $E_2$ at time $T_2$ when the voltage change is determined. The period between times $T_1$ and $T_2$ is, of course, predetermined by the program of the microprocessor.

The microprocessor is programmed to store the value $E_1$ and the value $E_2$ so that the total change of the potential on line 26, $\Delta E$, can be calculated to determine if it is greater than the predetermined minimum value which is expected for an intact electrode system. After the application of the negative test current during the period between $T_1$ and $T_2$, the test current is removed by the opening of the relay contact connecting junction 51 and line 56 and the potential on line 26, then decays exponentially toward the value $E_1$, indicative of the pH being measured by the electrode system. At some time during the decay the microprocessor energizes relay 58 to close its contact and apply as a result of the connection of the junction 30 and line 54 another current equal in magnitude and opposite in direction to the negative test current. That current which may be considered a positive test current causes the potential on line 26 to go from the value existing at the time of energization of relay 58 to a value $E_3$ which will differ from the voltage $E_1$ by the same magnitude as does the potential $E_2$ since the positive current is applied for the same time period as the negative test current. The relay 58 is then energized and the potential on line 26 decays back toward the value $E_1$ representing the potential produced by the electrode system as a result of the pH of the solution 20. The application of a reverse current through the electrode system serves to discharge any capacitance in the electrode being tested and it serves to prevent unidirectional ionic migration in the electrode glass.

As shown in FIG. 2 the pH of the solution 20 is periodically sampled by the microprocessor as at time $T_1$ and at time $T_5$. Subsequent sampling occurs at intervals similar to the interval between $T_1$ and $T_5$ and after a number of these intervals, the testing cycle is then repeated. Thus, for example, the intervals may be one-second intervals with the testing occurring in the first of each series of five consecutive one-second intervals. It is, of course, advantageous that the test current be modified as required by temperature changes at the electrode, etc. by appropriate actuation of a selected one of the relay 36 and 38 before each test of the electrode system.

Under some conditions it is possible that the pH being measured in the solution 20 instead of being steady at a value corresponding to the potential $E_1$, for example, may be varying as, for example, in a decreasing direction as shown by the line 70 during the period when the positive and negative test currents are applied. It is also possible that the magnitude of change between the time $T_1$ and the time $T_5$ shown as $X_V$ may be of such magnitude that the portion of the voltage change between $T_1$ and $T_3$, due to a change in pH, may cancel all or part of the voltage change during that period as a result of the application of the test current to the electrode system. Such an occurrence would cause the procedure as previously set forth to provide an indication of a defective electrode system when it is not defective in that there would be a net change in potential during the time of the application of the test current less than that required to indicate an intact electrode system. In order to overcome this possibility by one method, the potential on line 26 can have subtracted from it a potential change of an amount determined by the following expression:

$$X_V \left[ \frac{T_2 - T_1}{T_5 - T_1} \right]$$

In another method for overcoming this problem, the potential on line 26 is sampled both before and after the application of a negative test current and before and after the subsequent application of the current in the opposite direction which may be considered a positive test current. The order of the application of those test currents may, of course, be reversed. Thus, if $P_{T2}$ = the potential measured at time $T_2$ after a negative test current is applied, and $P_{T4}$ = the potential measured at time $T_4$ after a positive test current is applied, and if $RP$ = the potential on line 26 before the application of a test current then the quantity which must exceed a predetermined potential to indicate an intact electrode is the total change in potential as a result of both the negative and positive test currents which can be calculated by the expression $$[RP - P_{T2}] - [RP - P_{T4}]$$

and the predetermined potential is twice that value applicable when the potential change due to one test current only is used. The potential on line 26 during the application of the two opposite polarity test currents when pH is changing as shown by line 70 is illustrated in FIG. 2 by line 71.

The procedures set forth above as being executed by the microprocessor 10 can, of course, be executed manually as by the manual operation of the several contacts shown in FIG. 1, in appropriate sequence along with a timely reading of the potential at line 26 by means of a voltmeter for example, so that the potential on line 26 may be appropriately determined both before and upon the application of a test current to the electrode system to ascertain whether or not the voltage change is below a predetermined amount indicative of an intact electrode system.

What is claimed is:

1. A method for testing the integrity of the ion selective membrane of an ion selective electrode system while continuously measuring the concentration of said ion in a solution, comprising the steps of:
    passing a first current through said electrode system;
    passing a second current through said electrode system in an opposite direction to said first current and of magnitude and duration sufficient to cancel any charge remaining in said electrode system as a result of said first current; and
    measuring the total change in voltage across said electrode system as a result of the flow of current so that a measured voltage change to a value below that expected for an electrode system having an intact membrane indicates damage to said membrane.

2. The method of claim 1 in which the total change in voltage across said electrode system is a result of the flow of one of said first and second currents.

3. The method of claim 1 in which the total change in voltage across said electrode system is a result of the flow of both said first and second currents.

4. The method of claim 1, 2, or 3 in which the current for which the voltage change is measured is of a magnitude and duration such that for the existing temperature of the glass membrane it will produce across the electrode system at least a predetermined voltage change if the membrane is not damaged.

5. A method for testing the integrity of the ion selective membrane of an ion selective electrode system while continuously measuring the concentration of said ion in a solution, comprising the steps of:
    passing a test current through said electrode system, said test current being of a magnitude and duration such that for the existing temperature of the glass membrane it will produce at least a predetermined voltage change across the electrode system if the membrane is not damaged;
    measuring the change in voltage across said electrode system as a result of said test current flow so that a damaged membrane is indicated when said voltage change is less than said predetermined amount; and
    passing another current through said electrode system in an opposite direction to said test current to remove any effect on said electrode system caused by said test current.

6. A method for testing the integrity of the ion selective membrane of an ion selective electrode system while continuously measuring the concentration of said ion in a solution, comprising the steps of:
    passing a first test current through said electrode system, said test current being of a magnitude and duration such that for the existing temperature of the glass membrane it will produce at least a predetermined voltage change across the electrode system if the membrane is not damaged;
    measuring the change in voltage across said electrode system as a result of said first test current flow;
    passing a second test current of magnitude equal to said first test current through said electrode system in an opposite direction to said first test current and for the same duration;
    measuring the change in voltage across said electrode system as a result of said second test current flow; and
    subtracting said change in voltage due to said second test current from said change in voltage due to said first current so that a damaged membrane is indicated when the resulting difference is less than a predetermined amount.

7. In a pH measuring system which periodically samples the voltage output between a glass electrode and an associated reference electrode in a solution being measured, apparatus for testing the glass electrode between consecutive samples to determine if the glass membrane is cracked, comprising:
    means for passing a test current through said electrode combination for a period which is at least less than half the sampling period and for automatically passing another current of the same magnitude in the opposite direction for a period of the same duration as said test current; and
    means for measuring the voltage change between said reference and said glass electrode as a result of said test current for indicating a cracked electrode if said voltage change is below a minimum amount.

* * * * *